US005811453A

United States Patent [19]
Yanni et al.

[11] Patent Number: 5,811,453
[45] Date of Patent: *Sep. 22, 1998

[54] VISCOELASTIC COMPOSITIONS AND METHODS OF USE

[75] Inventors: John M. Yanni, Burleson; Gustav Graff, Cleburne, both of Tex.

[73] Assignee: Alcon Laboratories, Inc., Fort Worth, Tex.

[*] Notice: The term of this patent shall not extend beyond the expiration date of Pat. No. 5,607,966.

[21] Appl. No.: 768,747

[22] Filed: Dec. 17, 1996

Related U.S. Application Data

[63] Continuation-in-part of Ser. No. 368,718, Dec. 23, 1994, Pat. No. 5,607,966.

[51] Int. Cl.$^6$ .................. A61K 31/355; A61K 31/34
[52] U.S. Cl. ........................... 514/458; 514/469
[58] Field of Search ................. 514/458, 469

[56] References Cited

U.S. PATENT DOCUMENTS

| | | | |
|---|---|---|---|
| 4,374,258 | 2/1983 | Horner et al. | 549/407 |
| 4,988,728 | 1/1991 | Gerson et al. | 514/448 |
| 5,084,575 | 1/1992 | Kreft, III et al. | 546/172 |
| 5,166,331 | 11/1992 | della Valle et al. | 536/55.1 |
| 5,424,321 | 6/1995 | Hellberg et al. | 514/337 |

FOREIGN PATENT DOCUMENTS

| | | |
|---|---|---|
| 0 183 869 A1 | 6/1986 | European Pat. Off. |
| A-241043 | 10/1987 | European Pat. Off. |
| A-279867 | 8/1988 | European Pat. Off. |
| A-345592 | 12/1989 | European Pat. Off. |
| A-380367 | 8/1990 | European Pat. Off. |
| 0 387 771 A2 | 9/1990 | European Pat. Off. |
| 0 525 360 A2 | 2/1993 | European Pat. Off. |
| 0 527 458 A1 | 2/1993 | European Pat. Off. |
| 0 572 190 A1 | 12/1993 | European Pat. Off. |
| 0 640 609 A1 | 3/1995 | European Pat. Off. |
| 3407 507 A1 | 9/1985 | Germany . |
| A-3904674 | 8/1990 | Germany . |
| 58-072 579 A | 4/1983 | Japan . |
| 64-40484 A2 | 5/1989 | Japan . |
| 93/25187 | 12/1993 | WIPO . |
| WO 95/29906 | 11/1995 | WIPO . |
| 96/20187 | 7/1996 | WIPO . |
| 97/10236 | 3/1997 | WIPO . |

OTHER PUBLICATIONS

Eros, et al., Rheology and stability of Cremophor–containing creams. II. Study of cream stability., *Chemical Abstracts*, vol. 122, No. 22, Abstract No. 272753f (29 May 1995).

Rainsford, K. D., editor, "Volume 1: Inflammation Mechanisms and Actions of Tradtional Drugs", *Anti–Inflammatory and Anti–Rheumatic Drugs*, CRC Press, Inc., Boca Raton, Florida, pp. 54–68, 79–87, 120–126 and 140–144 (1985).

Bazan, H., "Response of Inflammatory Lipid Mediators following Corneal Injury", *Lipid Mediators In Eye Inflammation New Trends Lipid Mediators Res. Basel* Karger, vol. 5, pp. 1–11 (1990).

Bellavite, P., "The Superoxide–Forming Enzymatic System Of Phagocytes", *Free Radical Biology & Medicine*, vol. 4, pp. 225–261 (1988).

Bonne, C. et al., 2–(2–Hydroxy–4–methylphenyl)aminothiazole Hydrochloride as a Dual Inhibitor of Cyclooxygenase/Lipoxygenase and a Free Radical Scavenger, *Drug Research*, vol. 39(II), No. 10, pp. 1242–1250 (1989).

Campbell, W., "Lipid–Derived Autacoids: Eicosanoids And Platelet–Activiating Factor", *Goodman and Gilman's The Pharmacologial Basis Of Therapeutics*, Pergman Press, NY, pp. 600–617 (1990).

Chow, C., "Vitamin E And Oxidative Stress", *Free Radical Biology & Medicine*, vol. II, pp. 215–232 (1991).

Cohen, N. et al., "Lewis Acid Mediated Nucleophilic Substitution Reactions of 2–Alkoxy–3,4–dihydro–2H–Ibenzopyrans: Regiochemistry and Utility in the Synthesis of 3,4–Dihydro–2H–1–benzopyran–2–carboxylic Acids", *Journal of Organic Chemistry*, vol. 54, pp. 3282–3292 (1989).

Duchstein, H. et al., "Activated Species of Oxygen: A Challenge to Modern Pharmaceutical Chemistry", *Archives of Pharmacology*, vol. 325, pp. 129–146 (1992).

Duniec, Z. et al.; "Antioxidant properties of some chemicals vs their influence on cyclooxygenase and lipoxidase activities", *Biochemical Pharmacology*, vol. 32, No. 14, pp. 2283–2286 (1983).

Gifford, H., "On The Treatment Of Sympathetic Ophthalmia By Large Doses Of Salicylate Of Sodium, Aspirin, Or Other Salicylic Compounds", *Ophthalmoscope*, vol. 8, pp. 257–259 (1910).

Goa, K. et al., "Ocular Diclofenac", *Drugs & Aging*, vol. 2(6), pp. 473–486 (1992).

Graff, G. et al., "1–[4–3[4–[BIS(4–Fluorophenyl)Hydroxymethyl]–1–Piperidinyl]Propoxy]–3–Methoxyphenyl]Ethanone(AHR–5333): A Selective Human Blood Neutrophil 5–Lipoxygenase Inhibitor", *Prostaglandins*, vol. 38, No. 4, pp. 473–496 (1989).

Halliwell et al., "[1] Role of Free Radicals and Catalytic Metal Ions in Human Disease: An Overview", *Methods in Enzymology*, vol. 186, pp. 1–85 (1990).

(List continued on next page.)

*Primary Examiner*—Kimberly Jordan
*Attorney, Agent, or Firm*—Michael C. Mayo

[57] ABSTRACT

Compounds and methods for treating ocular tissues are disclosed. The methods utilize viscoelastic compositions containing certain compounds having an anti-inflammatory and anti-oxidant moiety covalently linked by an amide or ester bond. The compounds are useful in preventing and treating inflammatory and proliferative disorders through several mechanisms.

16 Claims, No Drawings

OTHER PUBLICATIONS

Hammond et al., "Antioxidant–based inhibitors of leukotriene biosynthesis. The discovery of 6–[1–[2–(hydroxymethyl)phenyl]–1–propen–3–yl]–2, 3–dihydro–5–benzofuranol, a potent topical antiinflammatory agent", *Journal of Medicinal Chemistry*, vol. 33, No. 3, pp. 908–918 (1990).

Hammond et al., "2,3–Dihydro–5–benzofuranols as Antioxidant–Based Inhibitors of Leukotriene Biosynthesis", *J. Med. Chem.*, vol. 32, pp. 1006–1020 (1989).

Hutchinson et al., "Drug Discovery and Development through the Genetic Engineering of Antibiotic–Producing Microorganisms", *Journal of Medicinal Chemistry*, vol. 32, No. 5, pp. 907–918 (1989).

Insel, P., "Analgesic–Antipyretics And Antiinflammatory Agents: Drugs Employed In The Treatment Of Rheumatoid Arthritis And Gout", *Goodman and Gilman's The Pharmacological Basis of Therapeutics*, Pergman Press, NY, pp. 638–669 and 681 (1990).

Lamba, O. et al., "Spectroscopic detection of lipid peroxidation products and structural changes in a sphingomyelin model system", *Biochimica et Biophysica Acta*, vol. 1081, pp. 181–187 (1991).

Momsen, W. et al., "Lipid Structural Reorganization Induced by the Pancreatic Lipase Cofactor, Procolipase", *Biochemistry*, vol. 34, pp. 7271–7281 (1995).

Nelson, P., "Cyclooxygenase Inhibitors", *CRC Handbook of Eicosanoids: Prostqaglandins and Related Lipids, vol. II, Drugs Acting Via the Eicosanoids*, CRC Press, Boca Raton, FL, pp. 59–133 (1989).

Pearce et al., "Inhibitors of Cholesterol Biosynthesis. 2. Hypocholesterolemic and Antioxidant Activities of Benzopyran and Tetrahydronaphthalene Analogues of the Tocotrienols", *Journal of Medicinal Chemistry*, vol. 37, No. 4, pp. 526–541 (1994).

Petty, M., et al.; "Protective effects of an α–tocopherol analogue against myocardial reperfusion injury in rats", *European Journal of Pharmacology*, vol. 210, pp. 85–90 (1992).

Sies, H., et al., "Role of tocopherols in the protection of biological systems against oxidative damage", *Journal of Photochemistry and Photobiology*, vol. 8, pp. 211–224 (1991).

Skoog, W. et al., "Studies on the Fibrinogn, Dextran and Phytochemagglutinin Methods of Isolating Leukocytes", *Blood*, vol. II, pp. 436–454 (1956).

Smaby, J. M. et al., "Characterization of Lipid Miscibility in Liquid–Expanded Monolayers at the Gas–Liquid Interface", *Langmuir*, vol. 8, No. 2, pp. 563–570 (1992).

Tseng, C. et al., "Inhibition of in Vitro Prostaglandin and Leukotriene Biosynthesis by Chinnamoyl–β–phenethylamine and N–Acyidopamine Derivatives", *Chem. Pharm. Bull.*, vol. 40, No. 2, pp. 396–400 (1992).

Vane, J. et al., "Inflammation and the mechanism of action of anti–inflammatory drugs", *FASEB Journal*, vol. 1, pp. 89–96 (1987).

VISCOELASTIC COMPOSITIONS AND METHODS OF USE

The present application is a continuation-in-part of U.S. patent application Ser. No. 08/362,718, filed Dec. 23, 1994, now U.S. Pat. No. 5,607,966.

BACKGROUND OF THE INVENTION

The present invention is directed to the provision of viscoelastic compositions containing compounds having potent anti-inflammatory, anti-oxidant and anti-proliferative activity. The present invention is also directed to various methods of using the compounds and compositions of the present invention in pharmaceutical applications including the treatment of inflammatory disorders such as ocular inflammation associated with ophthalmic disease and ophthalmic surgery.

Inflammation from cellular stress can cause excessive tissue damage. Numerous biochemical pathways are known to lead to inflammation. In general, these include the generation of locally produced or inflammatory cell derived proinflammatory cytokines (e.g., $IL_1$, $IL_6$, $IL_8$ and $TNF_\alpha$), as well as products from the cyclooxygenase system, such as prostaglandins, and the lipoxygenase system, such as leukotrienes, "HETEs" and "HPETEs." Such agents have been associated with inflammation. See generally, *Goodman and Gilman's The Pharmacological Basis of Therapeutics*, pages 600–617, Pergman Press, N.Y. (1990). Therapies designed to inhibit the production of these types of agents are therefore of great interest.

Non-steroidal anti-inflammatory agents (NSAIA) have been used for the treatment of inflammatory disorders. The following references may be referred to for further background concerning this use of NSAIAs:

*Ophthalmoscope*, volume 8, page 257 (1910);

*Nature* volume 231, page 232 (1971);

*FASEB Journal*, volume 1, page 89 (1987); and

*Inflammation and Mechanisms and Actions of Traditional Drugs*, Vol. I Anti-inflammatory and Anti-rheumatic drugs. Boca Raton, Fla., CRC Press, (1985).

However, there are some problems associated with NSAIA treatment including delivery to the appropriate site of action and side effects (*Goodman and Gilman's The Pharmacological Basis of Therapeutics* pages 638–669, Pergman Press, N.Y. (1990)).

Free radical molecules also play a major role in inflammation. These unstable chemical moieties lead to the oxidation of tissue resulting in damage. Such oxidative stress and damage has been described in *Biochemical Pharmacology*, 32(14), 2283–2286 (1983) and *Free Radicals in Biology and Medicine*, 4, 225–261 (1988). Agents that act as anti-oxidants can protect against oxidative damage. Such protection has been the subject of numerous scientific publications, including the following:

*Archives of Pharmacology*, volume 325, pages 129–146 (1992);

*Journal of Photochemistry and Photobiology*, volume 8, pages 211–224 (1991);

*Free Radicals in Biology and Medicine*, volume 11, pages 215–232 (1991); and

*European Journal of Pharmacology*, volume 210, pages 85–90 (1992).

The combination of anti-oxidant activity with other pharmacologically significant activities in a single molecule is discussed in JP 010484 A2 and EP 387771 A2; and compounds with cyclooxygenase/5-Lipoxygenase and anti-oxidant activity are discussed in *Drug Research*, 39(II) Number 10, pages 1242–1250 (1989). However, these references do not disclose the compounds of the present invention.

Ocular inflammation is a condition which generally causes patient discomfort including red eye, conjunctival edema and congestion, ocular discharge as well as scratchiness and itchiness. Ocular inflammation can be initiated by various insults. For example, ocular inflammation can result from allergic response to various allergens, bacterial infections, trauma to the eye, dry eye and surgical complications. Various anti-inflammatory therapies are currently in use for the treatment of ocular inflammation including the topical administration of diclofenac.

Ocular surgery can result in various post-surgical complications to the eye. Such complications generally include: 1) loss of vascular blood barrier function; 2) neutrophil accumulation; 3) tissue edema including conjunctiva swelling, conjunctiva congestion and corneal haze; 4) cataract formation; 5) cellular proliferation; and 6) loss of membrane integrity including decrease in docosahexaenoic acid levels in membrane phospholipids.

Cataracts are opacities of the ocular lens which generally arise in the elderly. In order to improve eyesight, the cataractous lens is removed and an intraocular lens is inserted into the capsular bag. In order to maximize the procedure and post-surgical recovery, viscoelastic materials are injected in the anterior chamber and capsular bag to prevent collapse of the anterior chamber and to protect tissue from damage resulting from physical manipulation. Various inflammatory responses and tissue damage, however, may still occur from such surgeries, as described above. There is a need, therefore, for the provision of improved viscoelastic compositions and methods which aid in the amelioration of inflammation, tissue damage and trauma-induced complications resulting from anterior segment surgery (e.g., cataract surgery and trabeculectomy).

Trabeculectomy, i.e., glaucoma filtration surgery, involves the surgical creation of a fistula with a conjunctival flap which allows the direct drainage of aqueous humor from the anterior chamber into the conjunctival tissue. This procedure is used as an alternative to drug therapy, and allows for an increase in outflow of aqueous humor, thereby lowering the elevated intraocular pressure associated with glaucoma. In order to maintain a deep chamber and enhance visualization during the surgery, viscoelastic compositions have been injected into the anterior chamber of the eye. Inflammatory responses resulting from the surgery, however, may cause complications. For example, many patients exposed to prior inflammatory episodes (e.g., uveitis, cataract extraction) have an increased incidence of "bleb" failure due to fibroplasia. With such complications, the filtration bleb becomes scarred or heals over so that aqueous drainage can no longer occur. Thus, a need exists for the provision of improved viscoelastic compositions which further decrease the inflammatory response, cellular damage, and proliferation resulting from glaucoma filtration surgery, permitting an increased longevity of the filtration bleb following surgery.

Vitrectomy surgery can also induce a variety of post-surgical complications. Many of these complications are further potentiated in diabetic patients who are at risk for many ocular pathologies. Due to the severity of the surgical procedure, the posterior segment surgery process can cause extensive tissue damage at both the acute and chronic phases of the recovery. Tissue edema generally occurs during the post-surgical acute phase. This is caused by breakdown of the blood aqueous and blood retinal barrier functions resulting in sustained vascular permeability and accumulation of plasma constituents in the ocular compartments following the surgical trauma. Ocular neovascularization may occur during the post-surgical chronic phase. The presence of elevated inflammatory and serum factors induce cell proliferation during the normal wound healing process. Slitlamp clinical examinations at 24 hours have indicated extensive anterior chamber flare and cell influx, conjunctiva congestion and swelling (with discharge), iritis, and corneal haze. See for example, Kreiger, A. E., Wound Complications In Pars Plana Vitrectomy, *Retina,* volume 13, No. 4, pages 335–344 (1993); Cherfan, G. M., et al., Nuclear Sclerotic Cataract After Vitrectomy for Idiopathic Epiretinal Membranes Causing Macular Pucker, *American Journal Of Ophthalmology* volume 111, pages 434–438 (1991); Thompson, J. T., et al., Progression of Nuclear Sclerosis and Long-term Visual Results of Vitrectomy With Transforming Growth Factor Beta-2 for Macular Holes, *American Journal Of Ophthalmology* volume 119, pages 48–54 (1995) and Dobbs, R. E., et al., Evaluation Of Lens Changes In Idiopathic Epiretinal Membrane, volume 5, Nos. 1 & 2, pages 143–148 (1988).

The chronic phase of the postsurgical period is characterized by more severe complications that can necessitate additional surgery. These include an incidence of recurrent retinal detachment, epiretinal proliferation, neovascular glaucoma, corneal problems, vitreous hemorrhage, cystoid macular edema, and occurrence of cataract formation within six months of surgery. While various surgical irrigating and viscoelastic compositions are employed, the frequency of above-described complications still needs to be lessened by facilitating the recovery of vascular leakage and limiting the duration of the cellular proliferative response. Therefore, a need exists to improve the current effectiveness of viscoelastic compositions used in vitrectomy surgery.

U.S. Pat. No. 5,480,914 (Meadows) describes the use of non-aqueous perfluorocarbon carriers to deliver various compounds to the eye. U.S. Pat. No. 5,166,331 (della Velle et al.) discloses the use of hyaluronic acid compositions to deliver various compounds to the eye. Neither of these references, however, disclose the compositions of the present invention. The present invention is directed to the provision of new viscoelastic compositions containing compounds that have potent anti-inflammatory, anti-oxidant and anti-proliferative activity in a single molecule. The use of a single chemical entity with these potent activities provides increased protection relative to the use of a compound with singular activity. The use of a single agent having both activities over a combination of these different agents in a viscoelastic composition provides uniform delivery of an active molecule, thereby simplifying issues of drug metabolism, toxicity and delivery.

SUMMARY OF INVENTION

The present invention provides methods of using novel compounds having potent anti-inflammatory, anti-oxidant and anti-proliferative activity for the treatment of inflammatory conditions, such as: 1) loss of vascular blood barrier function; 2) neutrophil accumulation; 3) tissue edema including conjunctiva swelling, conjunctiva congestion and corneal haze; 4) cataract formation; 5) cellular proliferation; and 6) loss of membrane integrity including decrease in docosahexaenoic acid levels in membrane phospholipids. The multi-therapeutic efficacies of the compounds of the present invention may act in an additive or synergistic manner in reducing cellular damage and inflammation. Additionally, the compounds of the present invention also exhibit other anti-inflammatory activity not present in the individual agents.

The viscoelastic compositions of the present invention contain these novel compounds. The compositions generally are comprised of various viscoelastic vehicles such as sodium hyaluronic acid, chondroitin sulfate, hydroxypropylmethylcellulose ("HPMC"), other naturally occurring or synthetics molecules and combinations thereof.

The compounds of the present invention include both a non-steroidal anti-inflammatory agent (NSAIA) moiety and an anti-oxidant moiety. The compounds of the present invention are therefore useful as cytoprotective agents. The compounds of the present invention also possess anti-proliferative activity. In order to provide effective therapy for inflammatory disorders, especially resulting from ocular surgery, the present invention takes advantage of these individual efficacies. In addition, the present invention improves upon these individual efficacies by providing greater drug delivery to the target tissues by means of administering a single drug having multiple therapeutic actions. The present invention also provides compounds that associate with lipid membranes, thus providing bioavailable anti-oxidant protection within lipid molecules susceptible to oxidation. Finally, the compounds of the present invention exhibit therapeutic properties which are not present in the individual moieties of the compounds. These and other advantages of the present invention will be apparent to those skilled in the art based on the following description.

The NSAIA component of the compounds provides anti-inflammatory activity when it is freed from the parent compound. The use of these NSAIAs will provide inhibition of cyclooxygenase, an important enzyme involved in the prostaglandin/inflammation pathway. Inhibition of the synthesis/release of pro-inflammatory cytokines also reduces the rate of wound healing and the occurrence of fibroplasia. The compounds also include an anti-oxidant component. As oxidative stress has been implicated in inflammatory responses, the presence of an anti-oxidant will further help treat the target tissue.

The compounds of the present invention also exhibit intrinsic properties present only in the combined molecule, not in the individual components. One such property is the inhibitory efficacy against 5-lipoxygenase, an enzyme known to be involved in inflammation.

Another advantage of the present invention is that the anti-inflammatory moiety and the anti-oxidant moiety are linked through an amide or ester bond. Since the carboxylic acid moiety of the NSAIA has been converted to an amide or ester, the resultant molecule is neutrally charged, thus increasing lipophilicity, and drug delivery. These compounds also associate with lipid membranes, thus providing resident antioxidant protection of these oxidizable biomolecules. Furthermore, amide or ester pro-drugs, may provide site-directed anti-inflammatory activity since amidases and esterases, components of the inflammatory response, will catalyze the hydrolysis of the amide or ester and release the non-steroidal anti-inflammatory agent and anti-oxidant.

The compounds of the present invention are capable of protecting against cellular damage by a wide range of insults. Since the compounds provide this protection by decreasing free radical or oxidative damage, reducing enzyme mediated inflammation, cellular proliferation, and improving site delivery, this therapy represents an improved multi-pronged approach to the treatment of inflammatory pathologies.

DETAILED DESCRIPTION OF INVENTION

The compounds of the present invention are of the formula (I):

$$A—X—(CH_2)_n—Y—(CH_2)_m—Z \qquad (I)$$

wherein:

A is a non-steroidal anti-inflammatory agent originally having a carboxylic acid;

X is O or NR;

A—X is an ester or amide linkage derived from the carboxylic acid moiety of the non-steroidal anti-inflammatory agent and the X;

R is H, $C_1$–$C_6$ alkyl or $C_3$–$C_6$ cycloalkyl;

Y, if present, is O, NR, $C(R)_2$, CH(OH) or $S(O)_{n'}$;

n is 2 to 4 and m is 1 to 4 when Y is O, NR, or $S(O)_{n'}$;

n is 0 to 4 and m is 0 to 4 when Y is $C(R)_2$ or is not present;

n is 1 to 4 and m is 0 to 4 when Y is CH(OH);

n' is 0 to 2; and

Z is:

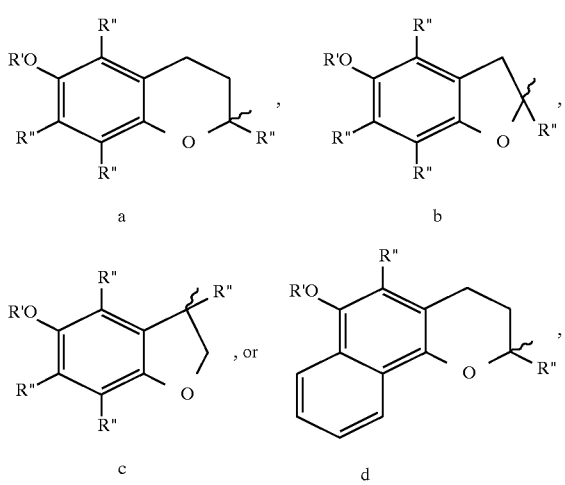

wherein:

R' is H, C(O)R, $C(O)N(R)_2$, $PO_3^-$, or $SO_3^-$; and

R" is H or $C_1$–$C_6$ alkyl.

The compounds of the present invention also include pharmaceutically acceptable salts of the compounds of formula (I).

The compounds of the present invention contain a non-steroidal anti-inflammatory agent, "A", having a carboxylic moiety. A number of chemical classes of non-steroidal anti-inflammatory agents have been identified. The following text, the entire contents of which are hereby incorporated by reference in the present specification, may be referred to for various NSAIA chemical classes: *CRC Handbook of Eicosanoids: Prostaglandins, and Related Lipids, Volume II, Drugs Acting Via the Eicosanoids*, pages 59–133, CRC Press, Boca Raton, Fla. (1989). The NSAIA may be selected, therefore, from a variety of chemical classes including, but not limited to, fenamic acids, such as flufenamic acid, niflumic acid and mefenamic acid; indoles, such as indomethacin, sulindac and tolmetin; phenylalkanoic acids, such as suprofen, ketorolac, flurbiprofen and ibuprofen; and phenylacetic acids, such as diclofenac. Further examples of NSAIAs are listed below:

| | | |
|---|---|---|
| loxoprofen | tolfenamic acid | indoprofen |
| pirprofen | clidanac | fenoprofen |
| naproxen | fenclorac | meclofenamate |
| benoxaprofen | carprofen | isofezolac |
| aceloferac | fenbufen | etodolic acid |
| fleclozic acid | amfenac | efenamic acid |
| bromfenac | ketoprofen | fenclofenac |
| alcofenac | orpanoxin | zomopirac |
| diflunisal | pranoprofen | zaltoprofen |

The preferred compounds are those wherein "A" is selected from the ester or amide derivatives of naproxen, flurbiprofen or diclofenac. The most preferred compounds are those wherein "A" is selected from the ester or amide derivatives of naproxen or flurbiprofen.

With respect to the other substituents of the compounds of formula (I), the preferred compounds are those wherein:

X is O or NR;

R is H or $C_1$–$C_3$ alkyl;

Y is CH(OH), and m is 0 to 2 and n is 1 or 2, or Y is not present, and m is 1 or 2 and n is 0 to 4;

Z is a, b or d;

R' is H or $C(O)CH_3$; and

R" is $CH_3$.

The most preferred compounds are those wherein:

X is O or NR;

R is H;

Y is CH(OH) or is not present;

m is 0 or 1;

n is 1;

Z is a, b, or d;

R' is H; and

R" is $CH_3$.

The following compounds are particularly preferred:

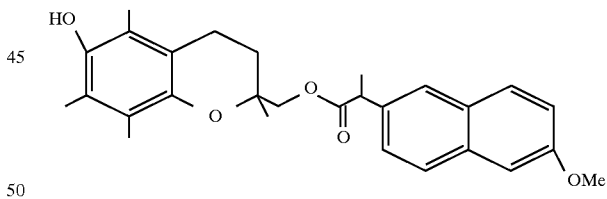

2-(6-hydroxy-2,5,7,8-tetramethyl-3,4-dihydro-2H-benzo[1,2-b]pyran-2-yl)methyl 2-(6-methoxy-2-naphthyl)propionate ("Compound B");

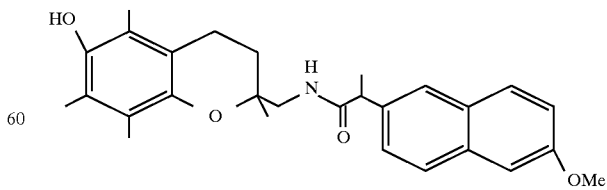

N-(2-(6-hydroxy-2,5,7,8-tetramethyl-3,4-dihydro-2H-benzo[1,2-b]pyran-2-yl)methyl) 2-(6-methoxy-2-naphthyl)propionamide ("Compound C");

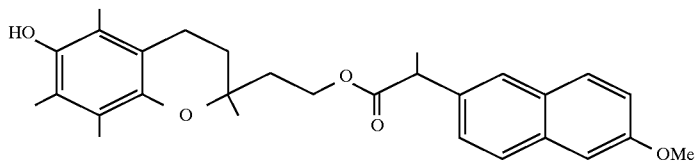

2-(6-hydroxy-2,5,7,8-tetramethyl-3,4-dihydro-2H-benzo[1,2-b]pyran-2-yl)ethyl 2-(6-methoxy-2-naphthyl)propionate ("Compound D");

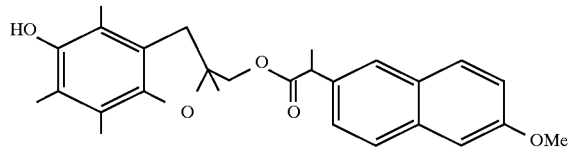

2-(5-hydroxy-2,4,6,7-tetramethyl-2,3-dihydro-benzo[1,2-b]furan-2-yl)methyl 2-(6-methoxy-2-naphthyl)propionate ("Compound E");

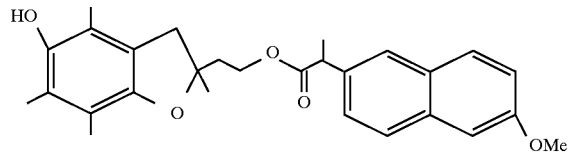

2-(5-hydroxy-2,4,6,7-tetramethyl-2,3-dihydro-benzo[1,2-b]furan-2-yl)ethyl 2-(6-methoxy-2-naphthyl)propionate ("Compound F"); and

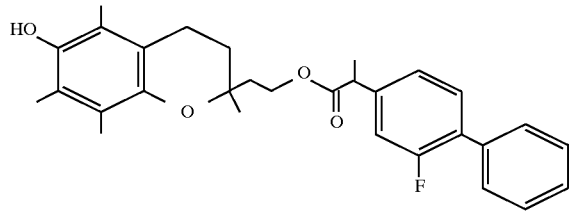

2-(6-hydroxy-2,5,7,8-tetramethyl-2,3-dihydro-2H-benzo[1,2-b]pyran-2-yl)ethyl 2-(3-fluoro-4-phenyl-phenyl)propionate ("Compound G").

The compounds of the present invention may be prepared by methods described in commonly assigned WIPO Publication No. 96/20187, the contents which are directed to synthetic schemes and methods are incorporated herein by reference.

The present invention is particularly directed to the provision of compositions adapted for treatment of inflammatory conditions. The compositions of the present invention will include one or more compounds of formula (I) and a pharmaceutically acceptable viscoelastic vehicle for said compound(s).

Viscoelastic agents which are useful in the compositions of the present invention include but are not limited to: sodium hyaluronate, chondroitin sulfate, polyacrylamide, HPMC, proteoglycans, collagen, methylcellulose, carboxymethyl cellulose, ethylcellulose, polyvinylpyrrolidone and keratan, all of various molecular weights and concentrations, or combinations thereof. Those skilled in the art will appreciate that the suitability of a given agent for a particular step in a surgical procedure will depend upon such things as the agent's concentration, average molecular weight, viscosity, pseudoplasticity, elasticity, rigidity, adherence (coatability), cohesiveness, molecular charge, and osmolality in solution. The agent's suitability will depend further on the function(s) which the agent is expected to perform and the surgical technique being employed by the surgeon. The concentration of the viscoelastic(s) in the compositions of the present invention will depend on various factors, as described below.

An appropriate buffer system (e.g., sodium phosphate, sodium acetate or sodium borate) may be added to prevent pH drift under storage conditions.

Some of the compounds of formula (I) may have limited solubility in water and therefore may require a surfactant or other appropriate co-solvent in the composition. Such co-solvents typically include: polyethoxylated castor oils, Polysorbate 20, 60 and 80; Pluronic® F-68, F-84 and P-103 (BASF Corp., Parsippany N.J., U.S.A.); cyclodextrin; or other agents known to those skilled in the art. Such co-solvents are typically employed at a level of from about 0.01 to 2 wt. %; however, it will be appreciated by those skilled in the art that these molecules may only be employed to the extent that they do not detrimentally affect the viscoelastic properties of the compositions of the present invention.

The viscoelastic compositions containing one or more compound of formula (I) may be used to treat patients afflicted with or prone to various types of cellular damage. In particular, these compositions may be used to treat inflammation where prostaglandins, leukotrienes, inflammatory cytokines and chemokines are known to participate. The concentrations of the compounds in the compositions will depend on various factors, including the nature of the condition to be treated with the compositions. The compounds and compositions of the present invention, however, will be used in a therapeutically effective amount. As used herein, a "therapeutically effective amount" is that amount required to prevent, reduce or ameliorate cellular inflammation, cellular damage and/or proliferation. Generally, the compositions may contain one or more of the compounds of the present invention in a concentration of from about 0.01 $\mu$M to about 100 $\mu$M.

As indicated above, compounds of formula (I) may be used to treat ocular inflammation at the cellular level and represents a particularly important aspect of the invention. In particular, the compounds are also useful in treating post-surgical complication resulting from ocular surgery. Treatment of the patient pre- or post-surgery with compounds of formula (I) may alleviate such conditions as tissue edema, neovascularization, conjunctiva swelling and congestion, fibroplasia (and scarring), corneal haze and cataract formation.

The methods of the present invention involve the use of various viscoelastic agents having different adherent or cohesive properties. Those skilled in the art will recognize that the compositions of the present invention may be employed by the skilled surgeon in a variety of surgical procedures.

Given the advantages of each type of viscoelastic, the surgeon may employ various viscoelastic compositions of the present invention in a single surgical procedure. U.S. Pat. No. 5,273,056 (McLaughlin et al.) discloses methods which exploit the use of different viscoelastic compositions during a given ocular surgery, the entire contents of which are incorporated herein by reference.

For portions of surgical procedures involving phacoemulsification and/or irrigation/aspiration, e.g., cataract surgery, it is generally preferable to use a viscoelastic agent that possesses relatively greater adherent properties and relatively lesser cohesive properties. Such viscoelastic agents are referred to herein as "adherent" agents. The cohesiveness of a viscoelastic agent in solution is thought to be dependent, at least in part, on the average molecular weight of that agent. At a given concentration, the greater the molecular weight, the greater the cohesiveness. The adherent agents, which are relatively lacking in cohesiveness, therefore will typically be of lower molecular weight; the molecular weight will typically be less than 1,000,000 daltons, preferably less than 750,000 daltons. To achieve a functionally desirable viscosity, the concentrations of the lower molecular weight agents in solution will need to be relatively higher than for higher molecular weight agents. These concentrations will typically be at least about 2% weight to volume (e.g. Occucoat®). The VISCOAT® product, for example, contains approximately 4% chondroitin sulfate (25,000 daltons) and 3% sodium hyaluronate (700,000 daltons). Vitrax® is believed to contain approximately 3% sodium hyaluronate (500,000 daltons). For agents such as these, which are being employed primarily for protective purposes as opposed to tissue manipulation purposes, a functionally desirable viscosity will be a viscosity sufficient to permit a protective layer of such agent to remain on the tissue or cells of concern during the surgical step(s) being performed. Such viscosity will typically be from about 3,000 cps to about 60,000 cps (at shear rate of 2 sec$^{-1}$ and 25 C), and preferably will be about 40,000 cps. Such adherent agents are capable of providing the protective function previously discussed, yet are not prone to inadvertent removal, which could jeopardize the delicate tissue being protected.

Those portions of surgical procedures involving manipulation of delicate tissue are generally better served by viscoelastic agents that possess relatively greater cohesive properties and relatively lesser adherent properties. Such agents are referred to herein as "cohesive" agents. Typically, these cohesive agents will possess average molecular weights in excess of 1,000,000 daltons and will have functionally desirable viscosity at concentrations of not more than about 1.6% weight to volume. Examples of such cohesive agents are: the Provisc™ product, Healon®, Healon® GV, Amvisc® and Amvisc Plus®. For cohesive agents such as these, which are being employed primarily for tissue manipulation or maintenance purposes as opposed to protective purposes, a functionally desirable viscosity will be a viscosity sufficient to permit the skilled surgeon to use such agent as a soft tool to manipulate or support the tissue of concern during the surgical step(s) being performed. Such viscosity will depend upon the average molecular weight of the agent and its concentration in solution. Most preferred are cohesive agents having an average molecular weight of at least about 2,000,000 daltons and a concentration in solution of between about 1.0 to about 1.4% weight to volume. Such cohesive agents are capable of maintaining intraocular space and manipulating tissue without adhering to it. When their purpose has been served, they can, because of their cohesive properties, be readily removed with minimal trauma to the surrounding tissue.

The present invention may also be used in corneal transplant surgery. In conjunction with the removal of the patient's corneal button, it is desirable to replace the aqueous humor with a highly viscous agent that will provide a firm bed to support the donor cornea, yet be susceptible to easy removal upon completion of the surgery. The donor graft, on the other hand, requires maximum protection from the surgical trauma and should therefore be coated with a different, more adherent agent. Corneal transplant surgery also involves the risks of inflammation and cellular damage. Thus, the compositions of present invention are also useful in this type surgery.

The compositions of the present invention may also be used in posterior segment surgery. In a retinal detachment procedure, for example, a highly viscous, cohesive agent such as the Provisc™ product or Healon® GV will be used to manipulate the retina into position against the basement membrane of the choroid. Small amounts of an adherent agent, such as the VISCOAT® product, may be injected behind the retina before or after such manipulation to temporarily maintain the contact between the retina and basement membrane while more permanent attachment procedures well known to those skilled in the art are performed (e.g. tacking or laser welding).

The methods of the present invention are also directed to using the compositions of the present invention to ameliorate complications arising from glaucoma filtration surgery. Glaucoma filtration surgery involves the surgical creation of a fistula with a conjunctival flap which allows the direct drainage of aqueous humor from the anterior chamber into the conjunctival tissue thereby lowering the elevated intraocular pressure associated with glaucoma. However, in many patients, the filtration "bleb" becomes scarred or healed over so that aqueous drainage can no longer occur. In order to maintain a deep chamber and enhance visualization during the surgery, the viscoelastic compositions of the present invention will be injected into the anterior chamber of the eye. The addition of these compositions will ameliorate inflammatory conditions resulting from the surgery, fibroplasia and decrease bleb failure.

EXAMPLE 1

The following study illustrates the usefulness of compositions of the present invention in glaucoma filtration surgery.

New Zealand albino (NZA) rabbits ranging in body weight from 2.5–3.0 kg were used as experimental animals for the glaucoma filtration surgery model. Following a preoperative ocular examination on the day of the operation, animals were placed under general anesthesia (ketamine HCl (45 mg/kg)/xylazine (6 mg/kg), s.c.). Topical ocular proparacaine HCl (ALCAINE®, Alcon Laboratories, Inc., Fort Worth, Tex.) was administered prior to the start of the surgical procedure to provide ocular analgesia.

A 5 mm superior limbal conjunctival incision was made along the corneal limbus and a conjunctival flap was created.

A Weck-Cel microsponge 2×2×2 mm in size (Weck, Research Triangle Park, N.C.) was saturated with 100 μL of either BSS PLUS® (Alcon), mitomycin C (0.5 mg/mL in BSS PLUS®), or test article and placed for 5 minutes between the conjunctiva and sclera to cover the appropriate area of the planned filtration site. The conjunctival wound was then rinsed with about 25 mL of BSS PLUS®. This process was immediately followed by a clear corneal paracentesis, a 2 mm sclerectomy, and an iridectomy. The corneal paracentesis was used to administer 1 mL of a surgical irrigation solution (e.g., BSS PLUS® or COMPOUND D TIS) into the anterior chamber for washing and removal of excess control or test agent administered to the subconjunctival wound. The corneal paracentesis site was also used to administer COMPOUND D, as described above, supplemented PROVISC® (Alcon) composition of the present invention (0.3 mL) to replace the aqueous humor. The conjunctival wound was then closed with 9-0 sutures.

Each study group consisted of 6 animals and received treatment as described in Table 1 below:

TABLE 1

Summary of Glaucoma Filtration Surgery Experimental Treatment Groups

| Study Group | Conjunctival Wound Treatment (sponge) | Anterior Chamber Irrigation | Anterior Chamber Fluid Replacement |
|---|---|---|---|
| I | BSS PLUS ® | BSS PLUS ® | BSS PLUS ® |
| II | Mitomycin C† | BSS PLUS ® | BSS PLUS ® |
| III | COMPOUND D TIS§ | COMPOUND D TIS | COMPOUND D-PROVISC ® ‡ |
| IV | Mitomycin C | COMPOUND D TIS | COMPOUND D-PROVISC ® |

†0.5 mg/mL in BSS PLUS ®
§Therapeutic Irrigation Solution consisting of BSS PLUS ® supplemented with COMPOUND D (0.5 μM) and cremophor EL (0.05%)
‡PROVISC ® supplemented with COMPOUND D (0.5 μM) and cremophor EL (0.05%)

Postoperative assessment of bleb vascularity was conducted with conscious animals. Measurement of bleb size was carried out under general anesthesia (ketamine HCl/xylazine). Routine post-surgical examinations were conducted on days 1, 3, 5, 10, and 14 and every week thereafter until the time of bleb failure. Bleb failure was defined as a bleb score value of zero where the bleb score represents the sum of bleb size and height.

The number of functioning blebs through 8 weeks is reported in Table 2, below:

TABLE 2

| | Number of Functioning Blebs Post Operative Week | | | |
|---|---|---|---|---|
| Study Group | 1 wk | 2 wks | 4 wks | 8 wks |
| I | 0/6 | 0/6 | — | — |
| II | 6/6 | 6/6 | 6/6 | 4/6 |
| III | 6/6 | 2/6 | 1/6 | — |
| IV | 6/6 | 6/6 | 6/6 | 6/6 |

EXAMPLE 2

The following is an example of a preferred composition of the present invention:

| Ingredient | % w/v |
|---|---|
| Compound D | 0.000023 |
| Cremophor EL | 0.05 |
| Hyaluronic Acid, Sodium Salt | 1 |
| Dibasic Sodium Phosphate (Anhydrous) | 0.056 |
| Monobasic Sodium Phosphate (Monohydrate) | 0.004 |
| Sodium Chloride | 0.84 |
| Hydrochloric Acid | pH adjusted |
| Sodium Hydroxide | pH adjusted |
| Water | QS |

EXAMPLE 3

The following is an example of a viscoelastic composition of the present invention wherein "Compound" denotes a compound of the present invention:

| Ingredient | % w/v |
|---|---|
| Compound | 0.00001–0.0010 |
| Cremophor EL | 0.05 |
| Sodium Chondroitin Sulfate | 4.0 |
| Sodium Hyaluronate | 3.0 |
| Sodium Dihydrogen Phosphate, Monohydrate | 0.045 |
| Disodium Hydrogen Phosphate, Anhydrous | 0.2 |
| Sodium Chloride | 0.310 |
| Water | QS |
| Hydrochloric Acid | pH adjusted |
| Sodium Hydroxide | pH adjusted |

What is claimed is:

1. A viscoelastic composition comprising a pharmaceutically acceptable viscoelastic vehicle and an amount of a compound of the following formula effective to decrease inflammation, free radical/oxidative damage or cellular proliferation in mammalian tissues;

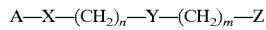

wherein:

A is a non-steroidal anti-inflammatory agent originally having a carboxylic acid moiety;

X is O or NR;

A—X is an ester or amide formed from the carboxylic acid moiety and the X;

R is H, $C_1$–$C_6$ alkyl or $C_3$–$C_6$ cycloalkyl;

Y, if present, is O, NR, $C(R)_2$, CH(OH) or $S(O)_{n'}$;

n is 2 to 4 and m is 1 to 4 when Y is O, NR, or $S(O)_{n'}$;

n is 0 to 4 and m is 0 to 4 when Y is $C(R)_2$ or is not present;

n is 1 to 4 and m is 0 to 4 when Y is CH(OH);

n' is 0 to 2; and

Z is selected from the group consisting of:

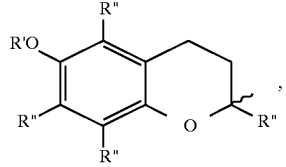

a

-continued

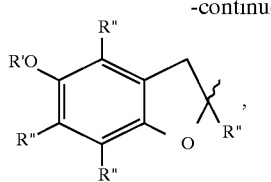

b

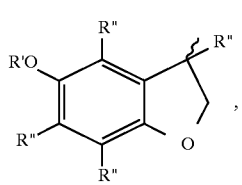

c

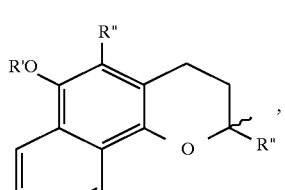

d wherein:

R' is H, C(O)R, C(O)N(R)$_2$, PO$_3^-$ or SO$_3^-$; and

R" is H or C$_1$–C$_6$ alkyl;

and a pharmaceutically acceptable salt thereof.

2. The composition according to claim 1, wherein the viscoelastic vehicle is comprised of sodium hyaluronate, chondroitin sulfate, HPMC or combinations thereof.

3. The composition according to claim 1, wherein the viscoelastic vehicle is comprised of cremophor El, hyaluronic acid sodium salt, dibasic sodium phosphate, monobasic sodium phosphate, sodium chloride, hydrochloric acid, sodium hydroxide and water.

4. The composition according to claim 1, wherein:
R is H or C$_1$–C$_3$ alkyl;
Y is CH(OH), m is 0 to 2, and n is 1 or 2, or Y is not present, m is 1 or 2, and n is 0 to 4;
Z is a, b or d;
R' is H, C(O)CH$_3$; and
R" is CH$_3$.

5. The composition according to claim 1, wherein the non-steroidal anti-inflammatory agent is selected from the group consisting of: fenamic acids, indoles, and phenylalkanoic acids.

6. The composition according to claim 1, wherein the non-steroidal anti-inflammatory agent is selected from the group consisting of:
loxoprofen; tolfenamic acid; indoprofen; pirprofen; clidanac; fenoprofen; naproxen; fenclorac; meclofenamate; benoxaprofen; carprofen; isofezolac; aceloferac; fenbufen; etodolic acid; fleclozic acid; amfenac; efenamic acid; bromfenac; ketoprofen; fenclofenac; alcofenac; orpanoxin; zomopirac; diflunisal; flufenamic acid; niflumic acid; mefenamic acid; pranoprofen; zaltoprofen; indomethacin; sulindac; tolmetin; suprofen; ketorolac; flurbiprofen; ibuprofen; and diclofenac.

7. The composition according to claim 1, wherein the non-steroidal anti-inflammatory agent is selected from the group consisting of naproxen, fluribiprofen and diclofenac.

8. The composition according to claim 1, wherein the compound is selected from the group consisting of:

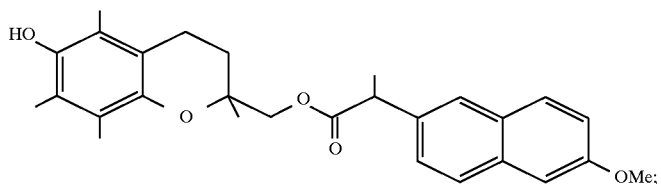

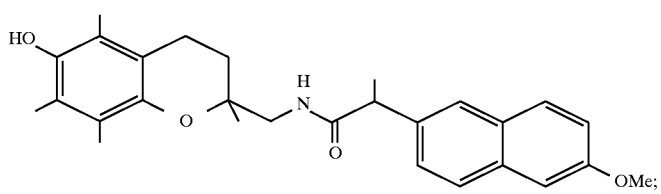

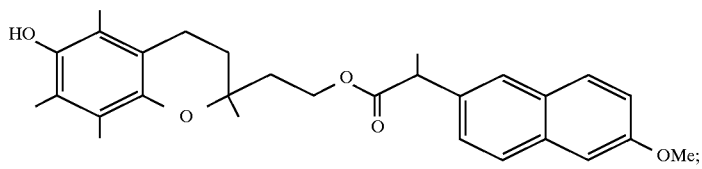

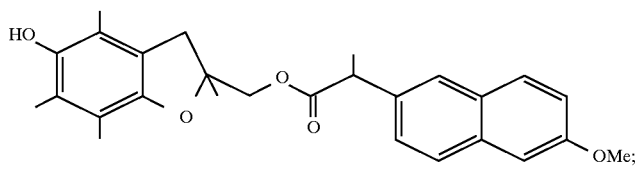

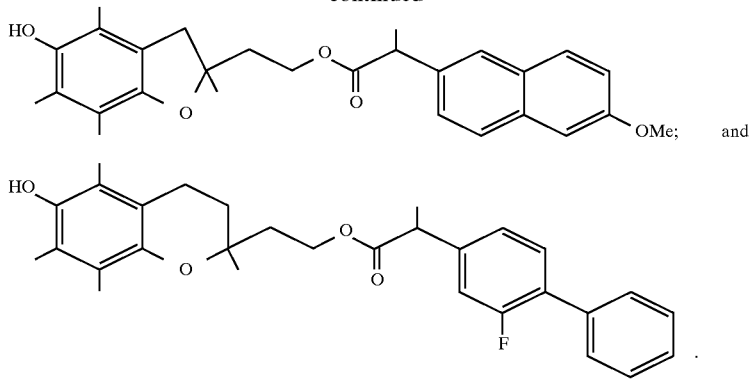

9. A method of preventing or alleviating inflammation, free radical/oxidative damage or cellular proliferation of mammalian tissue which comprises administering to a mammal a therapeutically effective amount of a viscoelastic composition comprising a pharmaceutically acceptable viscoelastic vehicle and an amount of a compound of the following formula effective to decrease inflammation, free radical/oxidative damage or cellular proliferation in said tissues:

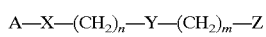

wherein:
A is a non-steroidal anti-inflammatory agent originally having a carboxylic acid moiety;
X is O or NR;
A—X is an ester or amide formed from the carboxylic acid moiety and the X;
R is H, $C_1$–$C_6$ alkyl or $C_3$–$C_6$ cycloalkyl;
Y, if present, is O, NR, $C(R)_2$, CH(OH) or $S(O)_{n'}$;
n is 2 to 4 and m is 1 to 4 when Y is O, NR, or $S(O)_{n'}$;
n is 0 to 4 and m is 0 to 4 when Y is $C(R)_2$ or is not present;
n is 1 to 4 and m is 0 to 4 when Y is CH(OH);
n' is 0 to 2; and
Z is selected from the group consisting of:

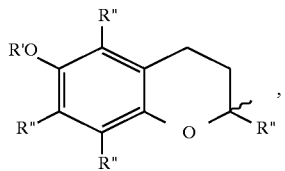

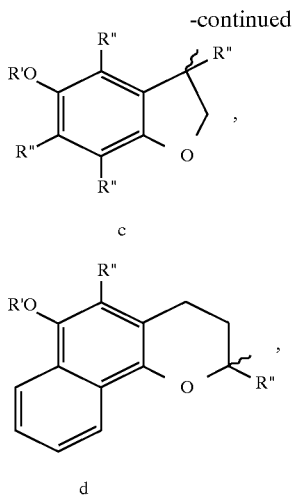

wherein:
R' is H, C(O)R, $C(O)N(R)_2$, $PO_3^-$ or $SO_3^-$; and
R" is H or $C_1$–$C_6$ alkyl;
and a pharmaceutically acceptable salt thereof.

10. The method according to claim 1, wherein the viscoelastic vehicle is comprised of sodium hyaluronate, chondroitin sulfate, HPMC or combinations thereof.

11. The method according to claim 1, wherein the viscoelastic vehicle is comprised of cremophor El, hyaluronic acid sodium salt, dibasic sodium phosphate, monobasic sodium phosphate, sodium chloride, hydrochloric acid, sodium hydroxide and water.

12. The method according to claim 9, wherein:
R is H or $C_1$–$C_3$ alkyl;
Y is CH(OH), m is 0 to 2, and n is 1 or 2, or Y is not present, m is 1 or 2, and n is 0 to 4;
Z is a, b or d;
R' is H, $C(O)CH_3$; and
R" is $CH_3$.

13. The method according to claim 9, wherein the non-steroidal anti-inflammatory agent is selected from the group consisting of: fenamic acids, indoles, and phenylalkanoic acids.

14. The method according to claim 9, wherein the non-steroidal anti-inflammatory agent is selected from the group consisting of:
loxoprofen; tolfenamic acid; indoprofen; pirprofen; clidanac; fenoprofen; naproxen; fenclorac; meclofenamate;

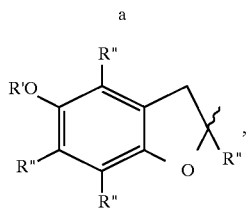

benoxaprofen; carprofen; isofezolac; aceloferac; fenbufen; etodolic acid; fleclozic acid; amfenac; efenamic acid; bromfenac; ketoprofen; fenclofenac; alcofenac; orpanoxin; zomopirac; diflunisal; flufenamic acid; niflumic acid; mefenamic acid; pranoprofen; zaltoprofen; indomethacin; sulindac; tolmetin; suprofen; ketorolac; flurbiprofen; ibuprofen; and diclofenac.

15. The method according to claim 9, wherein the non-steroidal anti-inflammatory agent is selected from the group consisting of naproxen, flurbiprofen and diclofenac.

16. The method according to claim 9, wherein the compound is selected from the group consisting of:

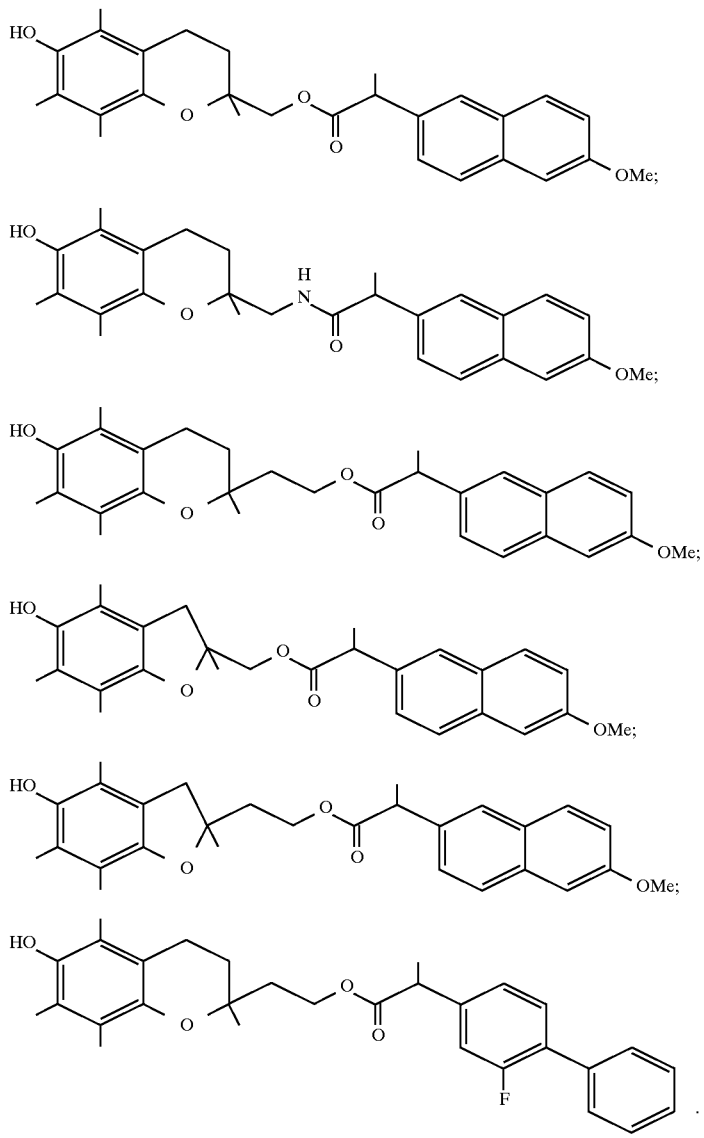

* * * * *

UNITED STATES PATENT AND TRADEMARK OFFICE
CERTIFICATE OF CORRECTION

PATENT NO : 5,811,453
DATED : 22 Sept. 1998
INVENTOR(S) : Yanni et al.

It is certified that error appears in the above-identified patent and that said Letters Patent is hereby corrected as shown below:

Title Page, Related U.S. Application Data, after Continuation-in-part of Ser. No. delete "368,718" and insert --362,718--.

Signed and Sealed this

Fifteenth Day of December, 1998

*Attest:*

BRUCE LEHMAN

*Attesting Officer*  *Commissioner of Patents and Trademarks*